United States Patent
Hsieh et al.

(10) Patent No.: US 6,976,975 B2
(45) Date of Patent: Dec. 20, 2005

(54) SAFETY SYRINGE

(75) Inventors: Hsin-Po Hsieh, Chian-Hwa Hsien (TW); Chi-Zer Ho, Taipei (TW); Shih-Chun Wang, Chia-Yi (TW)

(73) Assignee: Syriteck Medical Devices Co., Ltd., Taichung (TW)

( * ) Notice: Subject to any disclaimer, the term of this patent is extended or adjusted under 35 U.S.C. 154(b) by 232 days.

(21) Appl. No.: 10/683,432

(22) Filed: Oct. 14, 2003

(65) Prior Publication Data

US 2005/0080381 A1     Apr. 14, 2005

(51) Int. Cl.⁷ .............................................. A61M 5/00
(52) U.S. Cl. ..................................... 604/110; 128/919
(58) Field of Search .......................... 604/110, 187, 192, 604/198; 128/919

(56) References Cited

U.S. PATENT DOCUMENTS

| | | | | |
|---|---|---|---|---|
| 4,923,443 A * | 5/1990 | Greenwood et al. ........ | 604/110 |
| 5,401,246 A * | 3/1995 | Mazur et al. ................ | 604/110 |
| 5,462,531 A * | 10/1995 | Novacek et al. ............ | 604/110 |
| 5,520,649 A * | 5/1996 | Novacek et al. ............ | 604/110 |
| 5,820,605 A * | 10/1998 | Zdeb et al. ................. | 604/195 |
| 6,344,031 B1 * | 2/2002 | Novacek et al. ............ | 604/195 |
| 6,706,015 B2 * | 3/2004 | Bang .......................... | 604/110 |
| 2003/0212366 A1 * | 11/2003 | Bang .......................... | 604/196 |
| 2004/0082911 A1 * | 4/2004 | Tiu et al. .................... | 604/110 |

* cited by examiner

Primary Examiner—LoAn H. Thanh
(74) Attorney, Agent, or Firm—Rosenberg, Klein & Lee

(57) ABSTRACT

A safety syringe has a hollow barrel, a plunger, a connector, a plug and a needle hub. The plunger includes a socket to mount the connector. The connector has a needle connector protruded from the connector to connect with the needle hub. When the plunger is pushed toward the needle hub the first time, the needle hub of the connector is hidden in the socket and the plunger can not connect with the needle hub. When the plunger is pulled back and the syringe is full of medical solution, the needle hub of the connector protrudes from the socket. Pushing the plunger again toward the needle hub can connect the plunger and the needle hub together and the needle hub can retract back in the hollow barrel.

4 Claims, 8 Drawing Sheets

SAFETY SYRINGE

BACKGROUND OF THE INVENTION

1. Field of the Invention

The present invention relates to a syringe, and more particularly to a safety syringe that can retract the used needle.

2. Description of Related Art

A conventional syringe has a hollow barrel, a plunger and a needle hub. Due to contagious diseases, the needle of the syringe and even the hollow barrel and the plunger, should not be used again and should be discarded immediately after use. Also, to keep nurses, doctors or health workers who deal with discarded syringes from getting injured or infected by used needles, a safety syringe is needed. In particular, manufacturers have focused on syringes with retractable needles so that once the syringe has been used, the contaminated needle is entirely housed within the barrel whereby the chance of infection through accidental pricking is eliminated.

A conventional safety syringe disclosed in Taiwan Pat. No. 356013 comprises a hollow barrel, a plunger and a needle hub. The plunger has a connector formed on one end of the plunger to connect with the needle hub. The connector has a protrusion. The needle hub comprises a recess and an annular rib. The recess has a distal closed end and a proximal open end. The annular rib extends radially inward from the proximal open end of the recess. The protrusion of the connector can be clipped by the annular rib of the needle hub to connect the plunger and the needle hub together. When the plunger is pushed to the needle hub, the plunger with the connector becomes connected with the needle hub to retract the needle hub into the hollow barrel.

However, the conventional safety syringe often retracts the needle hub before use. Since the medical personnel will customarily push the plunger toward the needle hub to eject air before a medical solution is drawn into the safety syringe, the medical personnel often forgets that with the safety syringe the plunger can not be pushed to the front most end at this time. Thus, the plunger will connect with the needle hub and the needle hub will retract back in the hollow barrel. In this situation, the safety syringe can no longer be used and the safety syringe is wasted.

SUMMARY OF THE INVENTION

The main objective of the present invention is to provide a safety syringe that can pull back the used needle yet prevent the user from pulling back the needle before use.

To achieve the objective, a safety syringe in accordance with the present invention comprises a hollow barrel, a plunger, a connector, a plug and a needle hub. The hollow barrel comprises a distal annular rib formed inside the hollow barrel. The plunger comprises a socket to mount the connector. The connector comprises a needle connector protruded from the connector to connect with the needle hub. When the plunger is pushed toward the needle hub the first time, the needle hub of the connector is hidden in the socket and the plunger can not connect with the needle hub. When the plunger has been pulled back and the syringe is full of the medical solution, the needle hub of the connector will protrude from the socket by the distal annular rib. Pushing the plunger again toward the needle hub ejects the medicine into a patient and once the plunger meets and connects with the needle hub the combined plunger and needle hub can be retracted in the hollow barrel.

Further benefits and advantages of the present invention will become apparent after a careful reading of the detailed description with appropriate reference to the accompanying drawings.

DETAILED DESCRIPTION OF THE INVENTION

Figure 1:
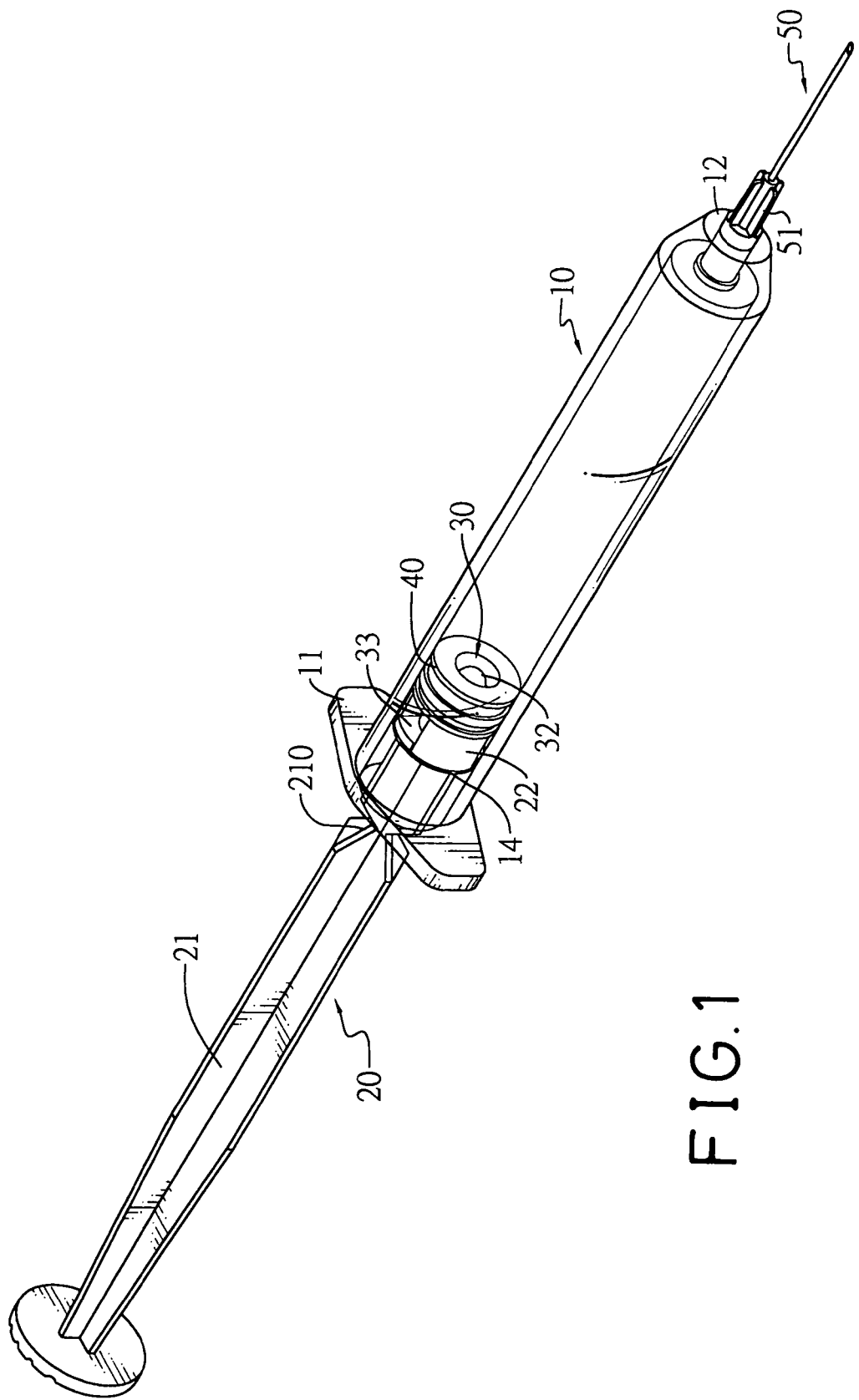
FIG. 1 is a perspective view of a safety syringe in accordance with the present invention.
Figure 2:
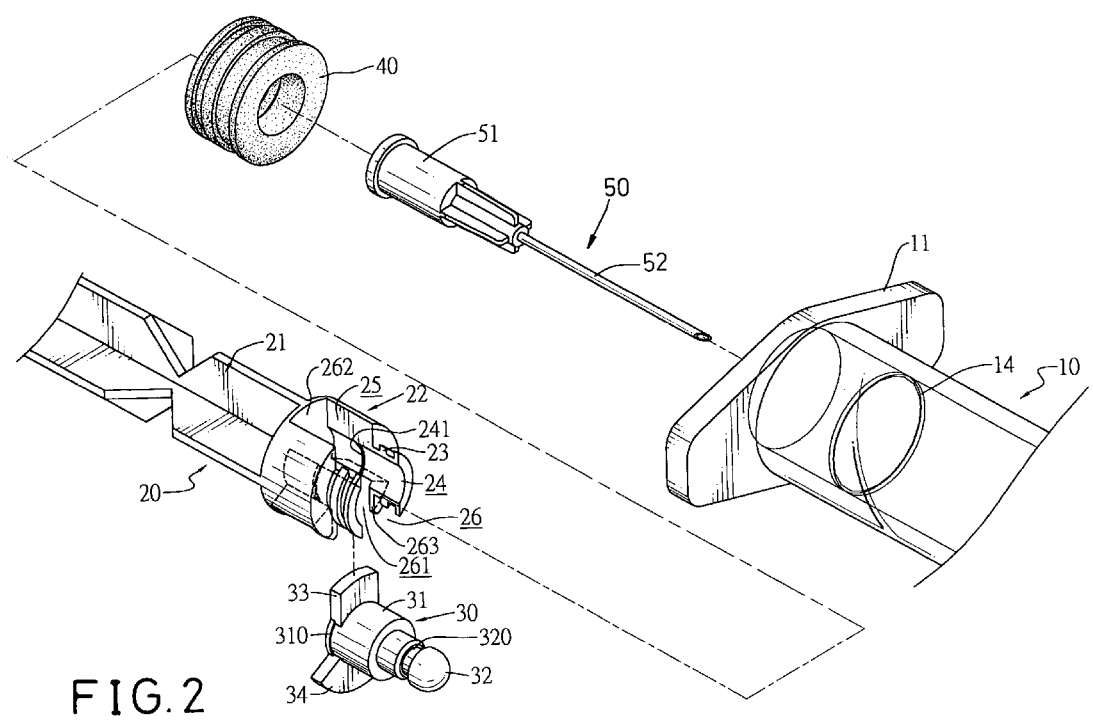
FIG. 2 is an exploded perspective view of the safety syringe in FIG. 1.

With reference to FIGS. 1 and 2, a safety syringe in accordance with the present invention comprises a hollow barrel (10), a plunger (20), a connector (30), a plug (40) and a needle hub (50).

The hollow barrel (10) is cylindrical and has a proximal open end (not numbered), a distal open end (not numbered), a lip (12), an inside surface (not numbered), an annular flange (11) and a distal annular rib (14). The lip (12) extends radially inward from the proximal open end of the hollow barrel (10) so the proximal open end (11) is smaller than the distal open end. The annular flange (11) extends radially out from the distal open end of the hollow barrel (10). The distal annular rib (14) is defined inside the hollow barrel (10) and near the distal open end. The distal annular rib (14) has an inner radius. Preferably, the distal annular rib (14) could be formed in non-continuous fragment.

The plunger (20) has a push rod (21), a socket (22) and a seal (not numbered), and is slidably mounted inside the hollow barrel (10). The push rod (21) has a proximal end (not numbered), a distal end (not numbered) and a peripheral side (not numbered). Preferably, the push rod (21) further comprises a V-shape groove (210) defined radially in the push rod (21). The seal is attached to the distal end of the push rod (21).

The socket (22) is formed on the proximal end of the push rod (21), and has a distal end, a proximal closed end (262), a longitudinal axis (not numbered), a sidewall (not numbered), a central chamber (24), a first slot (25), a second slot (26) and two recesses (261). The central chamber (24) is formed along the longitudinal axis of the socket (22) and has an inner wall (not numbered) and an annular rib (241). The annular rib (241) is formed radially on the inner wall of the central chamber (24) and near the distal end of the socket (22). The first slot (25) is formed in the sidewall of the socket (22) and communicates with the central chamber (24). The second slot (26) is formed in the sidewall of the socket (22), opposite to the first slot (25) and communicates with the central chamber (24). The two recesses (261) are formed in the sidewall of the socket (22) and in communication with the second slot (26), and form a positive limit (263) in the distal end of the socket (22). The two recesses (261) and the second slot (26) form a second chamber (not numbered). The second chamber is larger than the first slot (25). Preferably, the two recesses (261) are fan-shaped. More preferably, the socket (22) further comprises a protrusion (23) protruded from the distal end of the socket (22). The protrusion (23) has a radius smaller than that of the socket (22) and the central chamber (24) of the socket (22) extends through the protrusion (23). Furthermore, the radius of the socket (22) is smaller than the inner radius of the distal annular rib (14) in the hollow barrel (10).

The connector (30) is mounted into the socket (22) and has a body (31), an annular limiting rib (310), a needle connector (32), a first limiting protrusion (33) and a second limiting protrusion (34). The body (31) is cylindrical and mounted into the central chamber (24) of the socket (22), and has an outside surface (not numbered), a proximal end (not numbered) and a distal end (not numbered). The needle connector (32) extends from the distal end of the body (31). Preferably, a neck (320) is formed between the needle connector (32) and the body (31). The first limiting protrusion (33) and the second limiting protrusion (34) extend perpendicular outward from the proximal end of the body (31) and are defined corresponding to the first slot (25) and the second chamber of the socket (22) respectively. The first limiting protrusion (33) and the second limiting protrusion (34) each have an outer concentric circumference between an inner radius of the hollow barrel (10) and the distal annular rib (14) of the hollow barrel (10). The first limiting protrusion (33) and the second limiting protrusion (34) move freely in the first slot (25) and the second chamber respectively and between the proximal closed end (262) and the positive limit (263) of the socket (22). The annular limiting rib (310) extends radially outward from the proximal end of the body (31) and between the first limiting protrusion (33) and the second limiting protrusion (34). The connector (30) has a length slightly smaller than that of the central chamber (24) in the socket (22). The needle connector (32) will hide in the central chamber (24) of the socket (22) when the first limiting protrusion (33) and the second limiting protrusion (34) move freely between the proximal closed end (262) and the annular rib (241) of the socket (22). The needle connector (32) will protrude from the central chamber (24) of the socket (22) when the first limiting protrusion (33) and the second limiting protrusion (34) move freely between the annular rib (241) and the positive limit (263) of the socket (22).

The plug (40) is abutted to the distal end of the socket (22) on the plunger (20) and slidably mounted inside the hollow barrel (10). Preferably, the plug (40) is mounted around the protrusion (23) on the socket (22) of the plunger (20).

Figure 7:
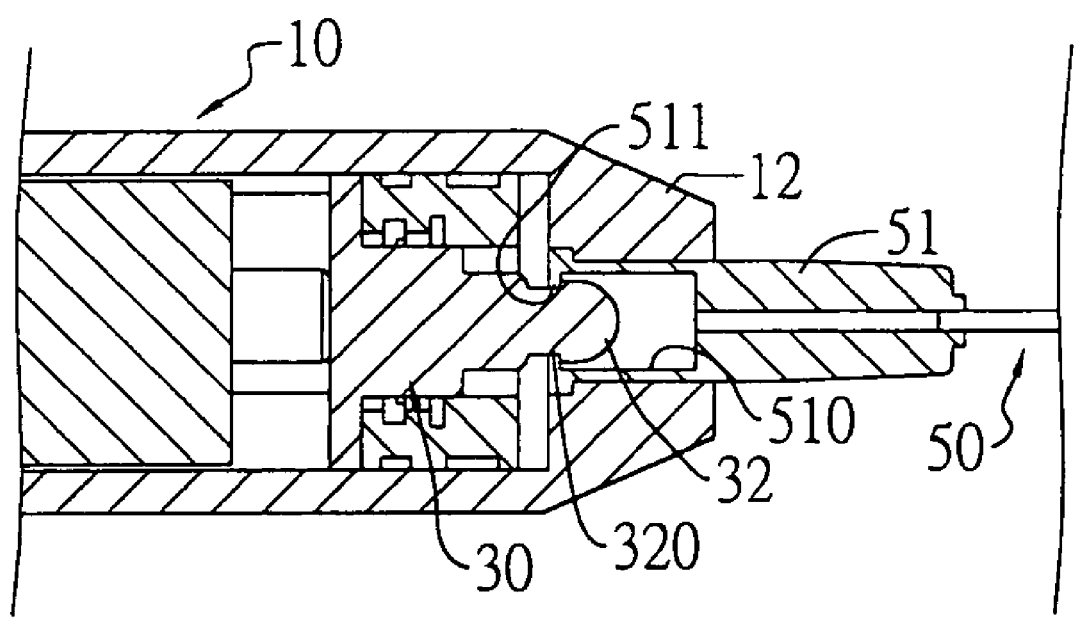
FIG. 7 is a cross sectional side plan view of the partial safety syringe in FIG. 5 showing the needle connector connected with a needle hub.

With further reference to FIG. 7, the needle hub (50) is mounted in the proximal open end of the hollow barrel (10) and has a connecting tube (51) and a needle (52). The connecting tube (51) has a distal end (not numbered), a proximal end (not numbered), a connecting chamber (510) and a proximal annular rib (511). The connecting chamber (510) is formed in the distal end of the connecting tube (51) and has a proximal open end. The connecting chamber (510) has a radius larger than that of the needle connector (32) of the connector (30). The proximal annular rib (511) extends radially inward from the proximal open end of the connecting chamber (510). The proximal annular rib (511) has an inner radius smaller than the radius of the needle connector (32) of the connector (30). The needle (52) is attached to the proximal end of the connecting tube (51) and has a central passage (not shown).

Figure 3:
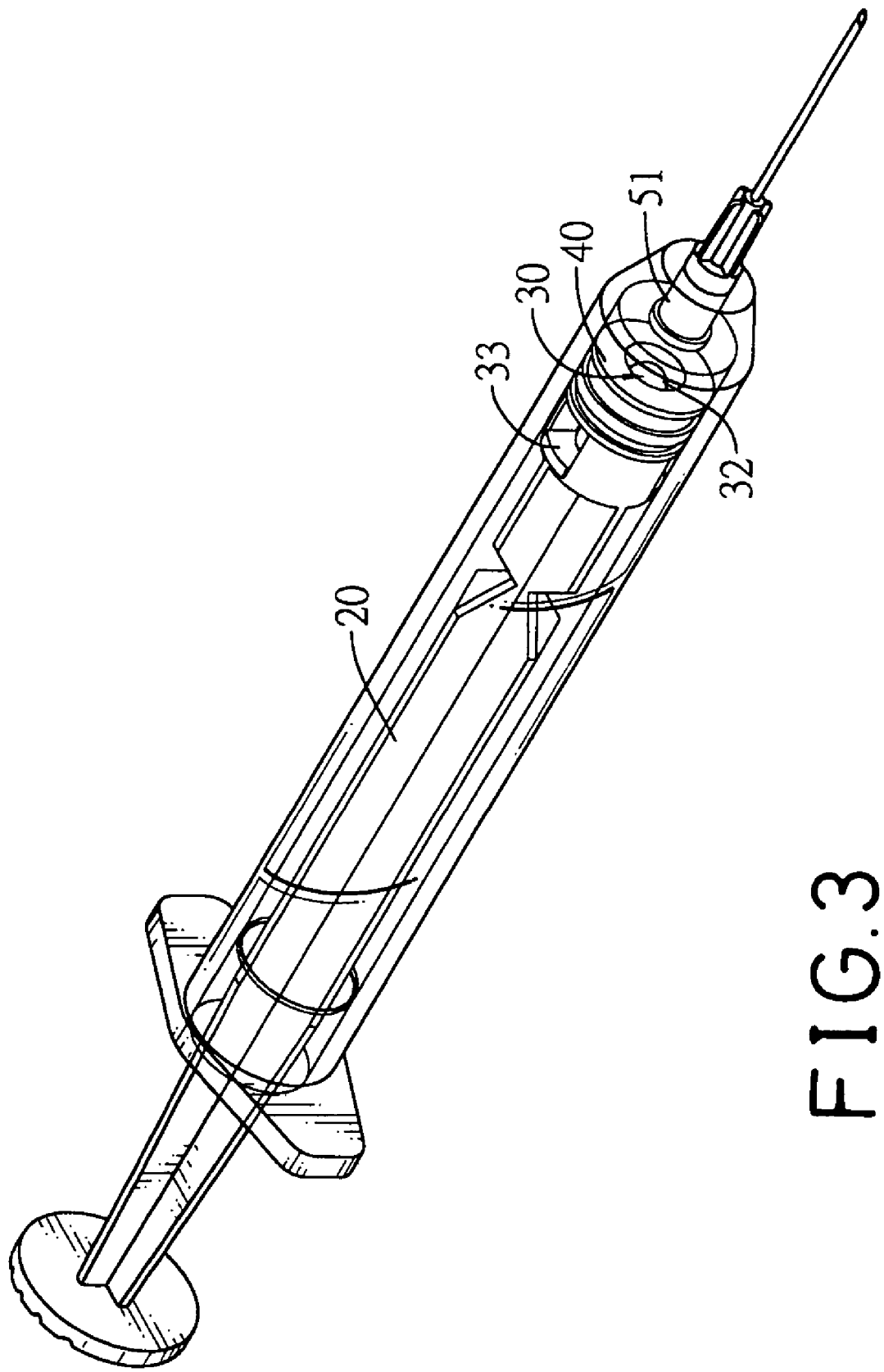
FIG. 3 is a perspective view of the safety syringe in FIG. 1 showing a plunger pushed into a hollow barrel in the first time.
Figure 4:
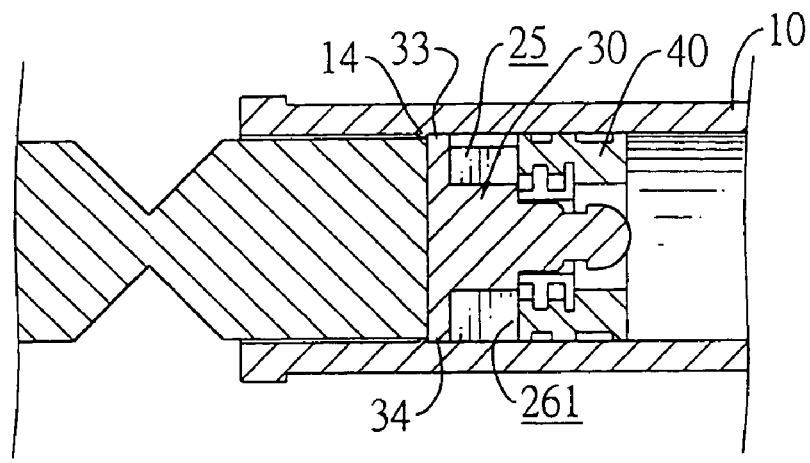
FIG. 4 is a cross sectional side plan view of the partial safety syringe in FIG. 1 showing the plunger pulled back from the hollow barrel.

With further reference to FIGS. 3 and 4, the plunger (20) with the connector (30) and the plug (40) will firstly extend into the hollow barrel (10) before using the safety syringe. When the plunger (20) is pushed toward the proximal open end of the hollow barrel (10), the first limiting protrusion (33) and the second limiting protrusion (34) will be blocked by the annular rib (14). Continuously pushing the plunger (20) will expand the annular rib (14) to let the first limiting protrusion (33) and the second limiting protrusion (34) pass through the annular rib (14) and to the proximal open end of the hollow barrel (10). In this situation, the needle connector (32) of the connector (30) is hidden in the central chamber (24) of the socket (22) so the needle connector (32) will not connect to the connecting tube (51) of the needle hub (50). After the plunger (20) is pushed to the proximal end of the hollow barrel (10), any air in the hollow barrel (10) is ejected. When the plunger (20) is pulled toward the distal open end of the hollow barrel (10), solution can be drawn through the needle hub (50) into the hollow barrel (10).

Figure 5:
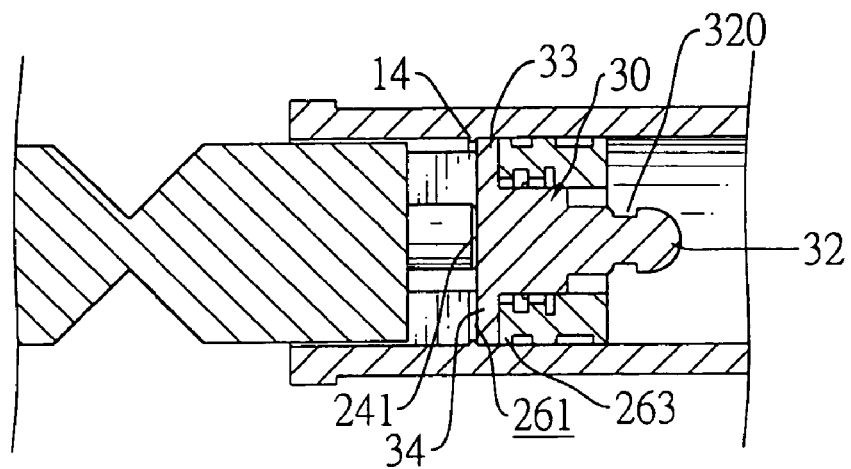
FIG. 5 is a cross sectional side plan view of the partial safety syringe in FIG. 1 showing a needle connector protruded from a socket of the plunger.
Figure 6:
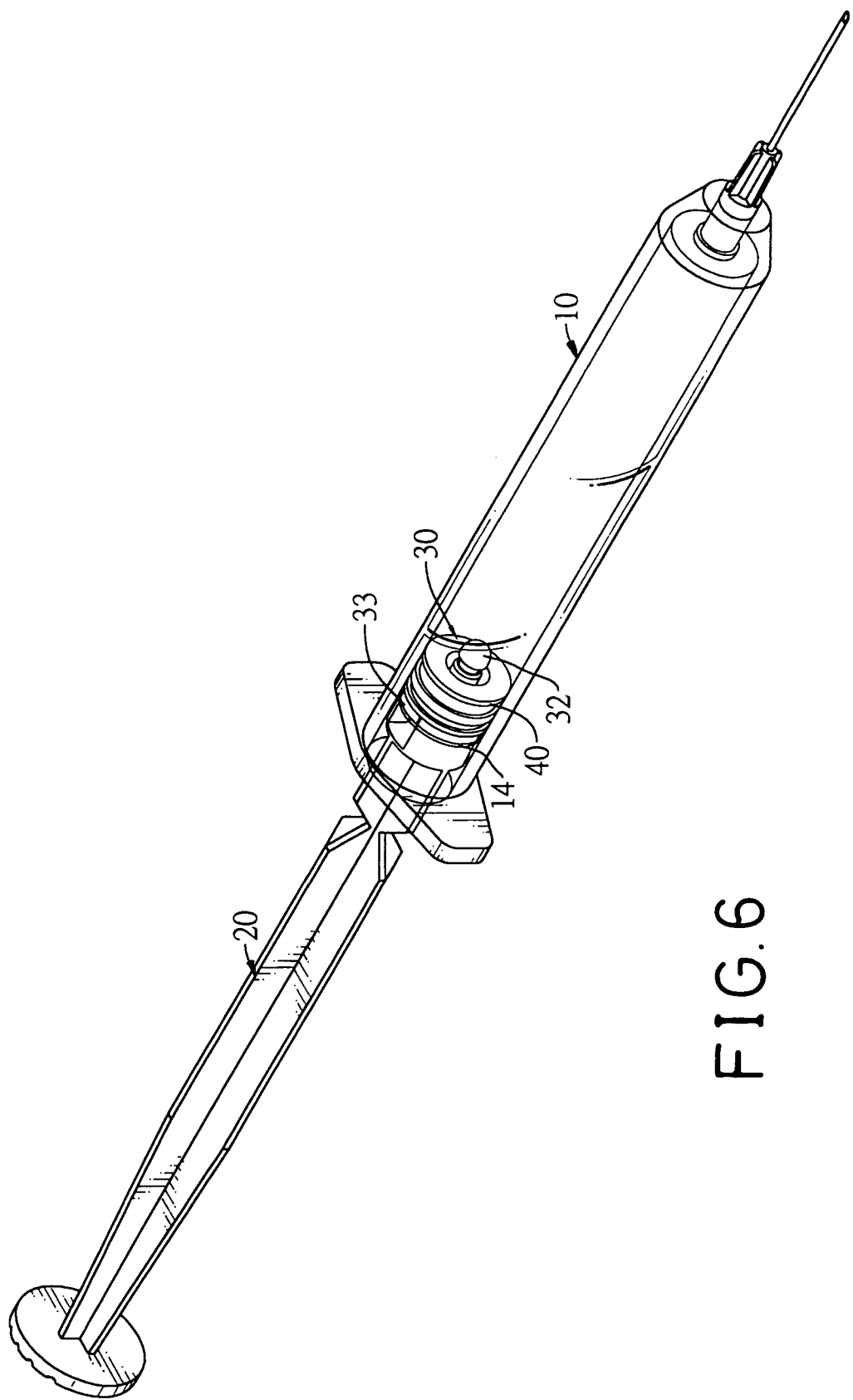
FIG. 6 is a perspective view of the safety syringe in FIG. 5 showing the needle connector protruded from the socket of the plunger.

With further reference to FIGS. 5 and 6, since the radiuses of the first limiting protrusion (33) and the second limiting protrusion (34) are larger than that of the distal annular rib (14) of the hollow barrel (10), the first limiting protrusion (33) and the second limiting protrusion (34) are blocked by the distal annular rib (14) of the hollow barrel (10). When pulling the plunger (20) continuously toward the distal open end of the hollow barrel (10), the annular rib (241) of the socket (22) passes through the first limiting protrusion (33) and the second limiting protrusion (34). The first limiting protrusion (33) and the second limiting protrusion (34) will move between the annular rib (241) and the positive limit (263). In this situation, the needle connector (32) and the neck (320) of the connector (30) protrude from the central chamber (24) of the socket (22).

With further reference to FIG. 7, the plunger (20) is pushed toward the proximal open end of the hollow barrel (10) again to eject the solution from the hollow barrel (10) into a patient. Since the needle connector (32) protrudes from the central chamber (24) of the socket (22), pushing the plunger (20) to the proximal open end of the hollow barrel (10) will let the needle connector (32) insert into the connecting chamber (510) of the connecting tube (51). The neck (320) of the needle connector (32) on the connector (30) is clipped by the proximal annular rib (511) of the connecting tube (51).

Figure 8:
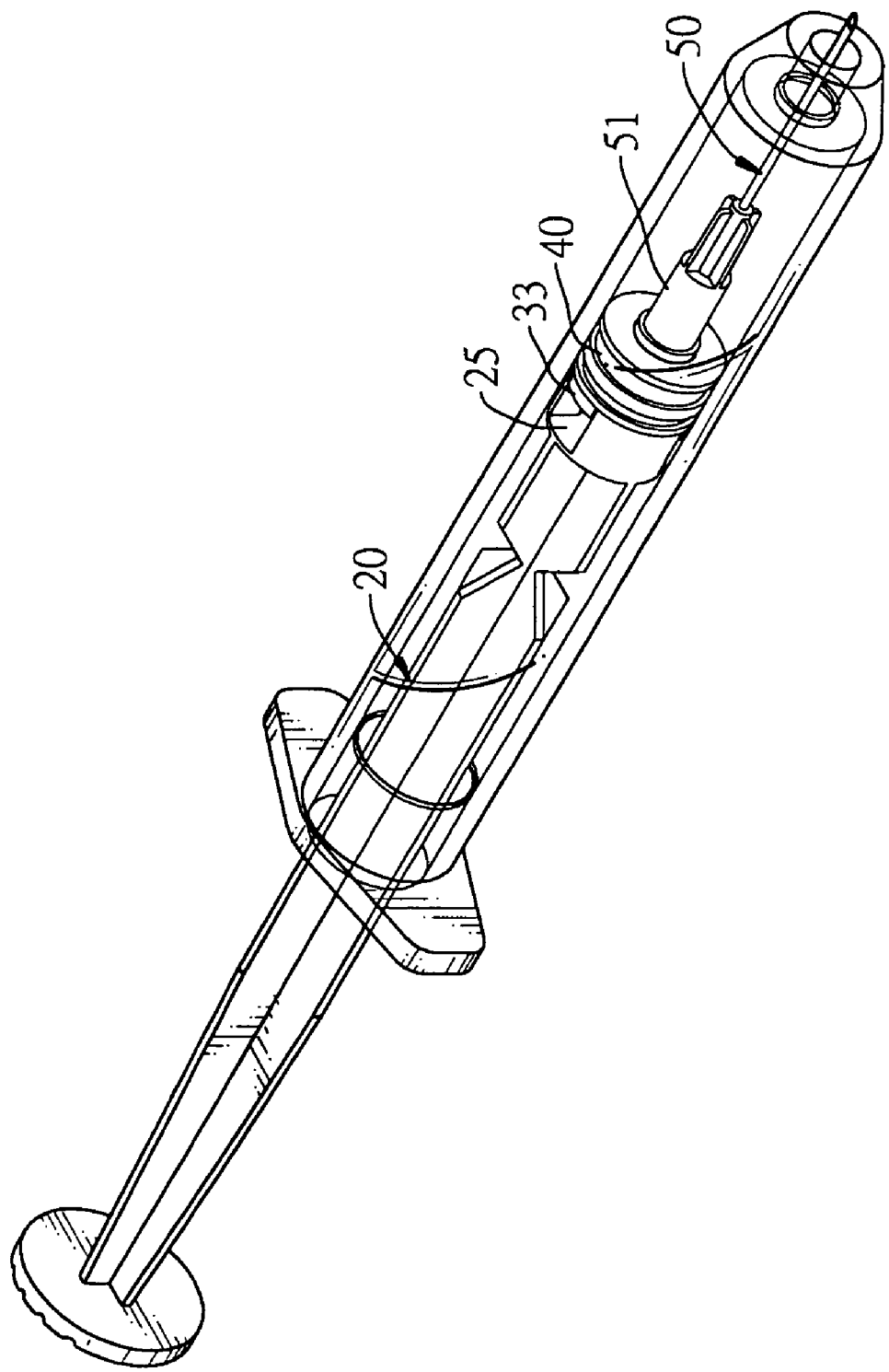
FIG. 8 is a perspective view of the syringe in FIG. 7 showing the needle hub retracted back into a hollow barrel.
Figure 9:
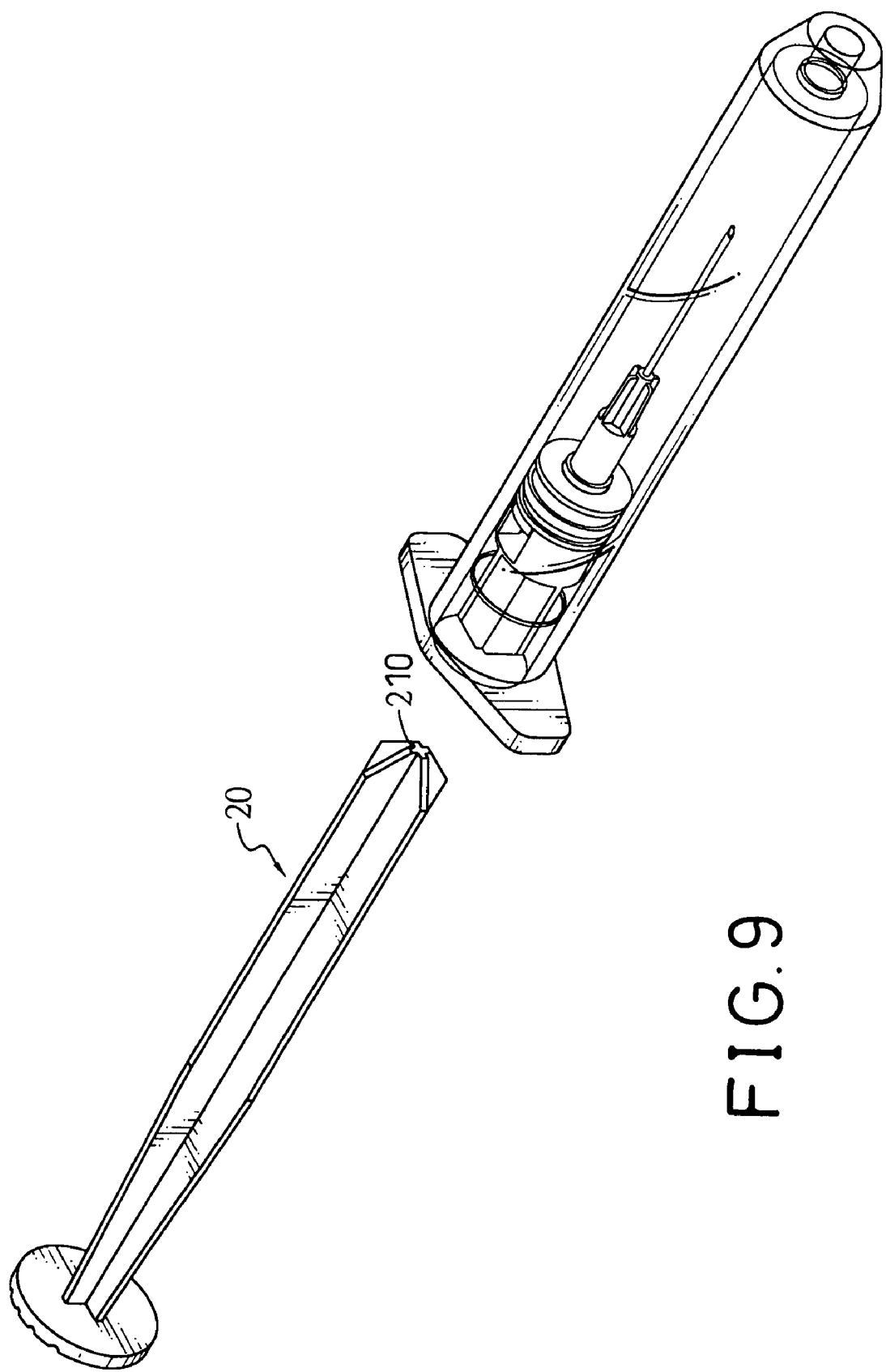
FIG. 9 is a perspective view of the syringe in FIG. 8 showing the plunger is broken and the needle hub is retained in the hollow barrel.

With further reference to FIGS. 8 and 9, the used needle (52) of the needle hub (50) is retracted into the hollow barrel (10) after use. Pulling the plunger (20) toward the distal open end of the hollow barrel (10) will pull the needle hub (50) back into the hollow barrel (10). After the groove (210) of the plunger (20) exits the hollow barrel (10), the groove (210) of the plunger (20) permits the protruding portion of the plunger (20) to be snapped off whereby the needle hub (50) is retained inside the hollow barrel (10).

The safety syringe in accordance with the present invention can allow the plunger (20) to travel into the hollow barrel (10) and not connect with the needle hub (50) in the first time. When the safety syringe has been used to treat a patient, the plunger (20) can connect with the needle hub (50) to let the needle hub (50) retract back in the hollow barrel (10). The present invention can avoid operating error and prevent wastage of syringes.

Although the invention has been explained in relation to its preferred embodiment, many other possible modifications and variations can be made without departing from the spirit and scope of the invention as hereinafter claimed is to be understood.

What is claimed is:

1. A safety syringe comprising:
   a hollow barrel having
      a proximal open end;
      a distal open end;
      an inside surface; and
      a distal annular rib defined inside the hollow barrel and near the distal open end, and having an inner radius;
   a plunger slidably mounted inside the hollow barrel and having
      a push rod having a proximal end, a distal end and a peripheral side; and
      a socket formed on the proximal end of the push rod and having a radius smaller than that of the distal annular rib in the hollow barrel, and having
         a distal end;
         a proximal closed end;
         a longitudinal axis;
         a sidewall;
         a central chamber formed along the longitudinal axis of the socket and having an inner wall and an annular rib formed on the inner wall of the central chamber and near the distal end of the socket;
         a first slot formed in the sidewall of the socket and communicated with the central chamber;
         a second slot formed in the sidewall of the socket, opposite to the first slot and communicated with the central chamber; and
         two recesses formed in the sidewall of the socket and in communication with the second slot, and forming a positive limit in the distal end of the socket, wherein the two recesses and the second slot form a second chamber larger than the first slot;
   a connector having a length slightly smaller than that of the central chamber in the socket and mounted into the socket, and having
      a cylindrical body mounted into the central chamber of the socket, and having an outside surface, a proximal end and a distal end;
      a first limiting protrusion extending perpendicular outward from the proximal end of the body, and defined corresponding to and moveably mounted in the first slot;
      a second limiting protrusion extending perpendicular outward from the proximal end of the body, and defined corresponding to and moveably mounted in the second chamber of the socket, wherein the first limiting protrusion and the second limiting protrusion each have an outer concentric circumference between that of the hollow barrel and the distal annular rib of the hollow barrel and moveable between the proximal closed end and the positive limit of the socket;
      an annular limiting rib extending radially outward from the proximal end of the body and between the first limiting protrusion and the second limiting protrusion; and
      a needle connector extending from the distal end of the body, wherein the needle connector is retained in the central chamber of the socket when the first limiting protrusion and the second limiting protrusion move freely between the proximal closed end and the annular rib of the socket and the needle connector protrudes from the central chamber of the socket when the first limiting protrusion and the second limiting protrusion move freely between the annular rib and the positive limit of the socket;
   a plug abutted to the distal end of the socket on the plunger and slidably mounted inside the hollow barrel; and
   a needle hub mounted in the proximal open end of the hollow barrel and having
      a connecting tube having
         a distal end;
         a proximal end;
         a connecting chamber formed in the distal end of the connecting tube and having a proximal open end, wherein the connecting chamber has a radius larger than that of the needle connector of the connector; and
         a proximal annular rib extended radially inward from the proximal open end of the connecting chamber, wherein the proximal annular rib has an inner radius smaller than that of the needle connector of the connector; and
      a needle attached to the proximal end of the connecting tube and having a central passage.

2. The safety syringe as claimed in claim 1, wherein the push rod further comprises a V-shape groove defined radially in the push rod.

3. The safety syringe as claimed in claim 1, wherein the socket further comprises a protrusion protruded from the distal end of the socket and has a radius smaller than that of the socket, and the central chamber of the socket extends through the protrusion and the plug is mounted around the protrusion on the socket of the plunger.

4. The safety syringe as claimed in claim 1, wherein a neck is formed between the needle connector and the body.

* * * * *